United States Patent [19]

Salee

[11] Patent Number: 5,424,519
[45] Date of Patent: Jun. 13, 1995

[54] MICROWAVED-ACTIVATED THERMAL STORAGE MATERIAL; AND METHOD

[75] Inventor: Gideon Salee, Dayton, Ohio

[73] Assignee: Battelle Memorial Institute, Columbus, Ohio

[21] Appl. No.: 124,931

[22] Filed: Sep. 21, 1993

[51] Int. Cl.$^6$ .............................................. H05B 6/80
[52] U.S. Cl. .................................. 219/759; 219/730; 426/109; 99/DIG. 14
[58] Field of Search ............... 219/730, 759; 426/107, 426/109, 241, 243; 128/399, 403; 99/DIG. 14

[56] References Cited

U.S. PATENT DOCUMENTS

| | | |
|---|---|---|
| D. 246,680 | 12/1977 | Sabol . |
| D. 306,543 | 3/1990 | Pestuglicci et al. . |
| D. 343,088 | 1/1994 | Owens . |
| D. 346,062 | 4/1994 | Owens . |
| 3,611,455 | 10/1971 | Gottfried . |
| 3,871,376 | 3/1975 | Kozak . |
| 3,872,525 | 3/1975 | Lea et al. . |
| 4,035,606 | 7/1977 | Browder . |
| 4,462,224 | 7/1984 | Dunshee et al. . |
| 4,538,630 | 9/1985 | Henderson .......................... 219/759 |
| 4,580,393 | 4/1986 | Furukawa . |
| 4,587,279 | 5/1986 | Slayer et al. . |
| 4,596,250 | 6/1986 | Beisong, III et al. . |
| 4,597,605 | 7/1986 | Gilbert . |
| 4,604,987 | 8/1986 | Keltner . |
| 4,617,322 | 10/1986 | Slayer . |
| 4,723,300 | 2/1988 | Aranow . |
| 4,743,726 | 5/1988 | Hughes et al. . |
| 4,756,311 | 7/1988 | Francis, Jr. . |
| 4,756,958 | 7/1988 | Bryant et al. . |
| 4,793,402 | 12/1988 | Yano et al. . |
| 4,825,939 | 5/1989 | Slayer et al. . |
| 4,843,662 | 7/1989 | Handelman . |
| 4,849,593 | 7/1989 | Hughes et al. ...................... 219/759 |

(List continued on next page.)

FOREIGN PATENT DOCUMENTS

| | | |
|---|---|---|
| 2037017 | 8/1991 | Canada . |
| 86-104758 | 1/1988 | China . |
| 309227 | 3/1989 | European Pat. Off. . |
| 412021 | 2/1991 | European Pat. Off. . |
| 63-217196 | 9/1988 | Japan . |
| 63-220864 | 9/1988 | Japan . |
| 63-317579 | 12/1988 | Japan . |
| 1006083 | 1/1989 | Japan . |
| 1006084 | 1/1989 | Japan . |
| 1075583 | 3/1989 | Japan . |
| 1123917 | 5/1989 | Japan . |
| 1217136 | 8/1989 | Japan . |
| 1236292 | 9/1989 | Japan . |
| 2052954 | 2/1990 | Japan . |
| 3047888 | 2/1991 | Japan . |
| 4039381 | 2/1992 | Japan . |
| 4222894 | 8/1992 | Japan . |
| 2252327 | 8/1992 | United Kingdom . |

OTHER PUBLICATIONS

Emulsion; In Encyclopedia of Chemical Technology: John Wiley & Sons; Third Edition; vol. 9; 1979; pp. 900–909.

Phase Change Fluids for Solar Thermal Systems; Sama, D. A., and Sladek, K. J.; In Fundamentals and Applications of Solar Energy—Part II; AIChE Symposium Series; vol. 77; No. 210; 1981; pp. 1–6.

LAVA Buns TM, Thermal Storage Heat Cushion, Photographs A-D, Vesture Corp.

*Primary Examiner*—Philip H. Leung
*Attorney, Agent, or Firm*—Klaus H. Wiesmann

[57] ABSTRACT

A thermal storage mixture activated by exposure to microwave energy is provided. The thermal storage mixture comprises a liquid phase of a microwave active fluid; and, a solid phase suspended within the microwave active fluid. The solid phase is preferably selected from material having a melting point at or below a temperature to which the liquid phase is heated, during use. The thermal storage mixture may be utilized in a container, to provide a thermal storage unit in a variety of applications. Herein, a thermal storage construction (heating construction) comprising a seat cushion having a thermal storage unit therein, to advantage, is described. Further, a process of storing thermal energy for release over an extended period of time is described.

20 Claims, 2 Drawing Sheets

U.S. PATENT DOCUMENTS

| | | |
|---|---|---|
| 4,914,717 | 4/1990 | Gibbon . |
| 4,925,241 | 5/1990 | Geraci . |
| 4,942,634 | 7/1990 | Saloff et al. . |
| 4,983,798 | 1/1991 | Eckler et al. . |
| 5,009,516 | 4/1991 | Geeck . |
| 5,044,031 | 9/1991 | Sherwood et al. . |
| 5,053,446 | 10/1991 | Salyer . |
| 5,067,771 | 11/1991 | Ellis . |
| 5,070,223 | 12/1991 | Colasante ............ 219/759 |
| 5,106,520 | 4/1992 | Slayer . |
| 5,175,031 | 12/1992 | Ochocki ............ 219/730 X |
| 5,211,949 | 5/1993 | Slayer . |
| 5,300,105 | 4/1994 | Owens . |

MICROWAVED-ACTIVATED THERMAL STORAGE MATERIAL; AND METHOD

FIELD OF THE INVENTION

The present invention relates to microwave-activated thermal storage materials. In particular, the invention concerns arrangements which are heated through exposure to microwave energy and which possess significant thermal storage ability and provide an advantageously slow release of heat over an extended period of time. Principles according to the present invention may be utilized, for example, in thermal heat cushions, foot and hand warmers, and as warmth extenders for foods. Also according to the present invention, methods relating to preparation and use of such arrangements are presented.

BACKGROUND OF THE INVENTION

Thermal storage arrangements (whether heated by exposure to microwave energy or otherwise) have been widely used for a variety of purposes. Those which are activated by microwave energy have been used, for example, as heat cushions. One such arrangement utilizes as a thermal storage unit an absorbent polyurethane foam substrate which is soaked with water and which is encased in a de-aerated bag. Water, a high specific heat substance, is the microwave-sensitive energy absorber in such a system. Upon exposure to microwave energy, the water absorbs the energy and heats up. The polyurethane foam homogenously spreads the water over a greater area. It also operates as an insulator, which retards dissipation of heat from the water.

A conventional system, utilizing as the thermal storage component a polyurethane foam soaked with water, generally comprises a foam seat cushion or the like with the thermal storage unit embedded therein. In preparation for use, the heat cushion is placed in a microwave oven and is exposed to microwave energy for several minutes. The unit then remains warm as the water cools and gives off its heat to the surrounding cushion.

A problem with such conventional arrangements is that even with the polyurethane foam insulation present to retard the dissipation of the heat, water, in its liquid state, is not a very good thermal storage material. When cooled, water will dissipate only sensible heat, which is the product of the temperature differential between the water and the area surrounding it, and its specific heat. Thus, to provide a large amount of heat, a large volume of water is needed.

SUMMARY OF THE INVENTION

According to the present invention a thermal storage mixture activatable by exposure to microwave energy is provided. Herein the term "activatable by exposure to microwave energy" is meant to indicate a mixture which, upon exposure to microwave energy of appropriate wave length, power and for a sufficient time, becomes heated, (i.e. stores thermal energy), and then slowly releases the heat over time. A thermal storage mixture according to the present invention may be utilized as part of a unit for warming a human, for example as in a seat cushion, a hand warmer, a foot warmer, or in a thermal blanket or cover; or, it may be used for a variety of other purposes. For example, to keep food warm.

The thermal storage mixture must include at least one component that is microwave active. There is no requirement that all components of the mixture be microwave active. The mixture may comprise, for example, a suspension or an emulsion. In preferred embodiments according to the present invention the mixture includes a liquid phase, and a phase which is solid at ambient of about 20° C.

Thermal storage mixtures (for example emulsions) according to the present invention generally comprise: a liquid phase of a microwave active fluid; and, a solid phase comprising particles suspended in the liquid phase. By the term "microwave active" in this context, it is meant that the phase absorbs microwave energy. In certain specific embodiments disclosed herein the solid phase is microwave inactive. By the term "microwave inactive" it is meant that the particles do not absorb microwave energy. In some embodiments the solid may be microwave active. In preferred emulsions, the liquid phase comprises water or a mixture of water with another fluid such as an alcohol (typically a $C_1$-$C_4$ alcohol), a glycol (typically $C_2$-$C_4$); a polymeric glycol such as PEG (polyethylene glycol); or, glycerol.

In preferred arrangements according to the present invention the solid phase comprises an organic wax material. While a variety of wax materials may be utilized, in preferred embodiments the wax material comprises a paraffin wax.

For preferred applications, the solid phase comprises a material having a melting point of at least 30° C., and preferably a material having a melting point no greater than about 90° C. In some preferred embodiments, for example, as a heat cushion, the solid phase should comprise a material having a melting point no greater than about 65° C., and preferably within the range of about 40°–60° C., most preferably 53°–57° C.

Also, according to the present invention a thermal storage unit which is activatable upon exposure to microwave energy is provided. The thermal storage unit generally comprises a microwave transparent container having an activatable emulsion as described, enclosed therein. The term "microwave transparent" in this context, is meant to refer to a container through which sufficient microwave energy can readily pass, to reach and be absorbed by the liquid phase of the emulsion. Preferred containers, for many applications, will comprise flexible pouches of polymeric material.

In preferred thermal storage units according to the present invention, a mechanical re-emulsifier is provided within the microwave transparent container, in contact with the fluid emulsion. The mechanical re-emulsifier may comprise, for example, compressible open cell material, such as a foam, sponge or rubber material. Preferred foams for utilization as such arrangements comprise elastomeric foams, for example polyurethane.

Also according to the present invention, a heating construction is provided which comprises a cover having a thermal storage unit as described above, enclosed therein. The cover may comprise materials appropriate to form a seat cushion, wherein heat is to be transferred to an external surface of the product; or, a thermal storage blanket, wherein the heat is to be retained underneath or within the arrangement. Preferably, portions of the heating construction should be sufficiently microwave transparent to permit enough microwave energy to pass through to the thermal storage unit, during use. Alternatively, the thermal storage unit can be activated and then enclosed in the heating construction.

Further, according to the present invention, a process of storing thermal energy for release over an extended period of time is provided. The term "extended period of time" in this context, is meant to refer to a period of time of sufficient length, for a purpose such as warming a product or maintaining a product warm. The term is also meant to refer to a more extended release than for the liquid phase if provided without the solid phase therein; and, it is meant to refer to a period of time extended by a phase change of an oil phase in the material. The process generally includes a step of exposing the emulsion to microwave energy of an appropriate power and for a sufficient period of time to heat the liquid phase of the emulsion to a temperature above the melting point of the solid phase of the emulsion; and, to melt the solid phase of the emulsion by thermal transfer from the liquid phase.

DETAILED DESCRIPTION OF THE INVENTION

The principles of the present invention, with respect to thermal storage units and arrangements, may be applied in a variety of systems. The systems may be used, for example, as sources of warmth for humans, for example, as seat cushions, foot warmers, hand warmers, etc. The principles of the present invention may, however, be applied in a variety of other systems as well, for example to provide a thermal blanket for food containers or other items to be kept warm. In the figures, a thermal storage unit according to the present invention is shown in the embodiment of the heat cushion. From the general principles described herein, application in a variety of other arrangements will be apparent.

Figure 1:
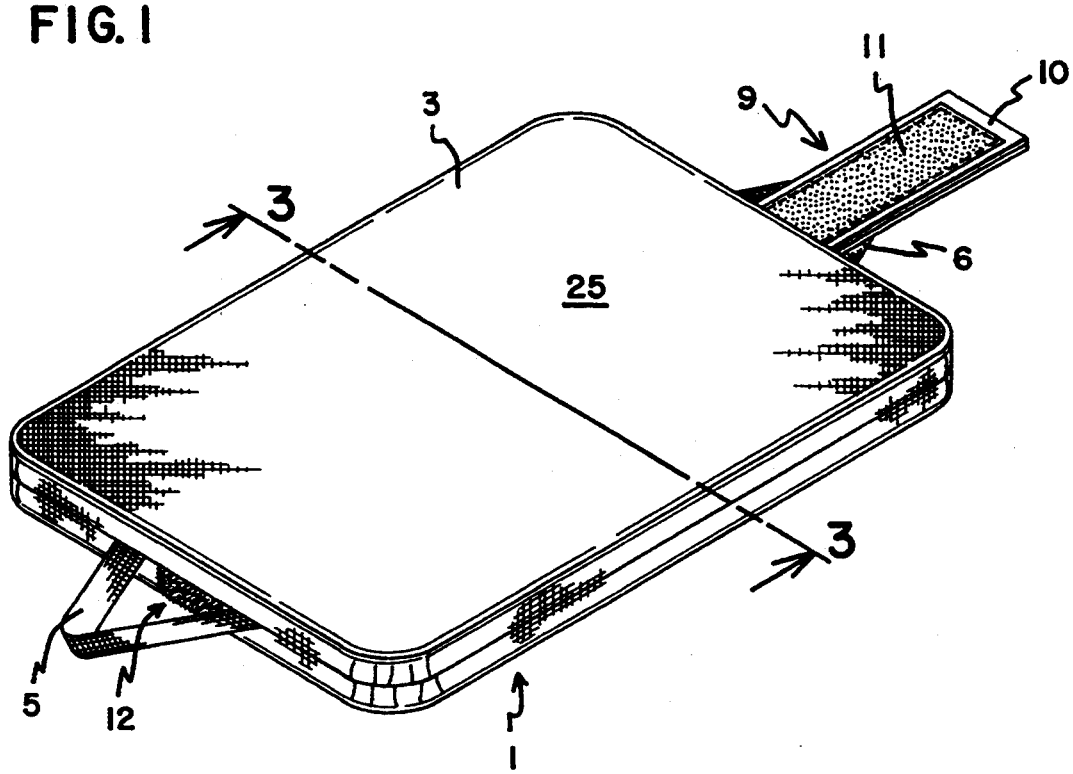
FIG. 1 is a perspective view of a seat cushion arrangement including features for thermal storage according to the present invention.

Reference numeral 1, FIG. 1, generally designates an arrangement or heating construction according to the present invention, including a thermal storage unit therein. Arrangement 1, FIG. 1, generally comprises a flexible seat cushion 3. The seat cushion 3 depicted is sufficiently flexible to be folded, and includes carrying handles 5 and 6, comprising, for example, polypropylene webbing or similar material. A closure arrangement to retain the cushion folded, when desired, is indicated generally at 9. The closure arrangement 9 depicted comprises a strap 10 including a first member 11 of a hook and loop closure system thereon. A second member 12 of the hook and loop closure system is indicated on, and underneath, the underside of the cushion 3, at 12. Thus, when cushion 3 is folded, strap 10 can be folded to engage section 11 with section 12 to retain the cushion 3 in a closed orientation. The hook and loop closure system may comprise, for example, the well-known system sold under the mark VELCRO®. Alternative closure arrangements, for example snaps, buckles, buttons or ties, may, of course, be used.

Figure 3:
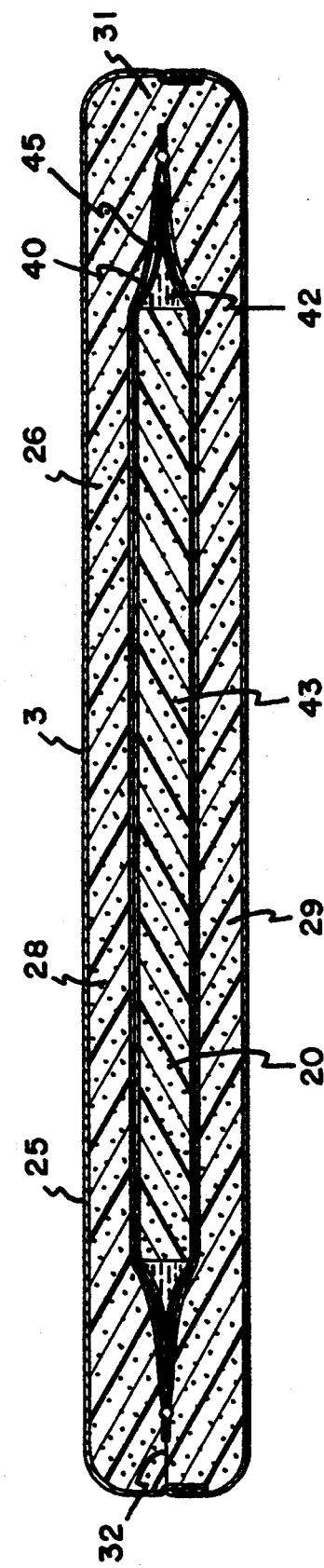
FIG. 3 is a cross-sectional view taken along line 3—3, FIG. 1.

Cushion 3 includes therein, according to the present invention, a thermal storage unit 20, FIG. 3. In operation, cushion 3 is exposed to microwave energy. After several minutes of exposure to the microwave energy, for example in a microwave oven, the cushion 3 will become relatively warm (a temperature of the thermal storage unit of around 35°–60° C. being typical). This effect is accomplished because cushion 3 includes, embedded therein, a thermal storage unit 20 according to the present invention.

In FIG. 3, a cross-sectional view of cushion 3 is depicted. Cushion 3 includes an outer cover or sheath 25, which encloses the various inner components. The sheath may comprise a fabric, for example, a fire retardant nylon. The inner components include foam pad 26 which surrounds thermal storage unit 20. More specifically, in the embodiment shown foam pad 26 includes first and second pads or walls 28 and 29, with thermal storage unit 20 positioned therebetween. Along edge 31, flaps 28 and 29 are integral with one another, i.e., they are merged continuously with no interface or seam. Along at least part of edge 32, on the other hand, flaps 28 and 29 can be separated, for insertion of thermal storage unit 20 during assembly. In preferred embodiments, foam pad 26 comprises a sheet of foam slit to form an envelope, such that thermal storage unit 20 can be readily inserted therein during assembly.

Still referring to FIG. 3, thermal storage unit 20 comprises a cover 40 having sealed therein a fluid mixture 42. In the particular embodiment shown, the mixture 42 is an emulsion enclosed in contact with a substrate 43. The substrate 43 preferably comprises an open-cell foam or sponge arrangement, substantially saturated with the fluid mixture 42. Preferred arrangements for this, and advantages derived therefrom, are discussed in further detail below.

Figure 2:
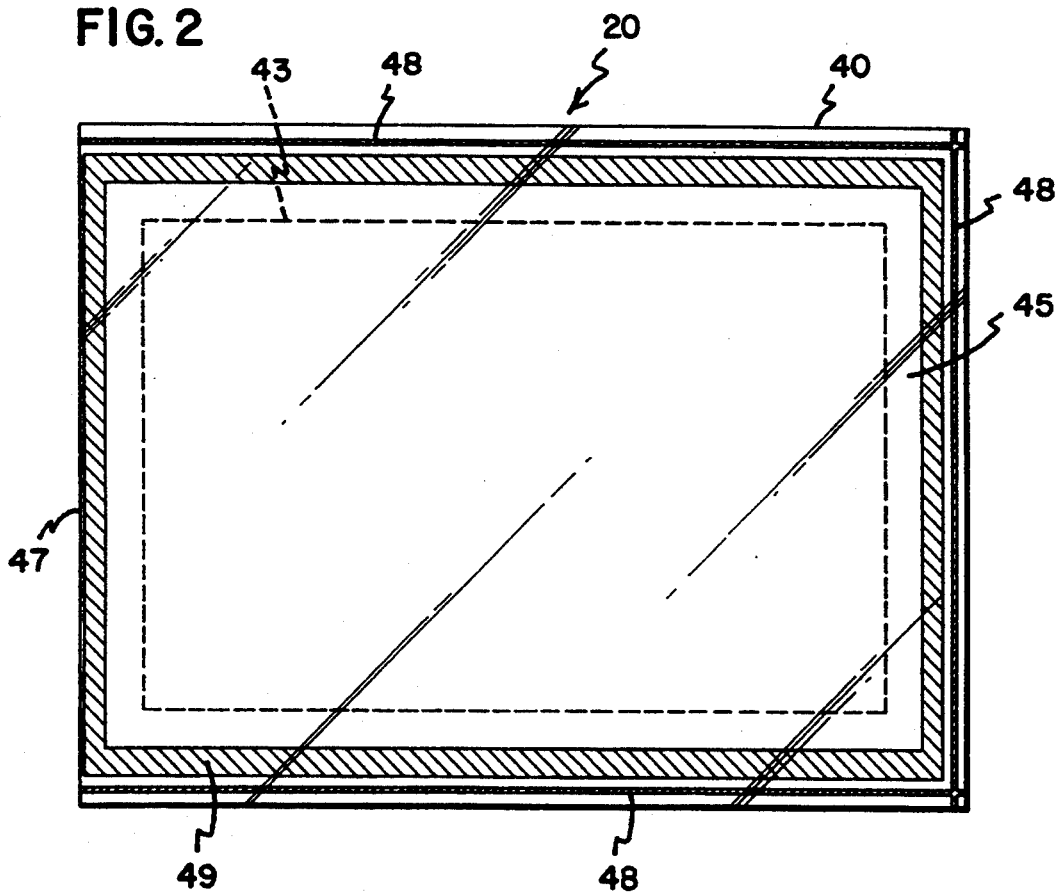
FIG. 2 is a top plan view of a thermal storage unit according to the present invention which may, for example, be utilized in the arrangement of FIG. 1.

A top plan view of the thermal storage unit 20 is depicted in FIG. 2. For the preferred arrangement shown in FIG. 2, thermal storage unit 20 includes first, outer, cover 40, and a second, inner cover 45. That is, cover 40 completely encloses cover 45. Alternately stated, thermal storage unit 20 is a "double bag" arrangement, with cover 40 sealing a second cover 45 for security. This is advantageous, since material received within second cover 45 will, upon exposure to microwave energy, become relatively hot; and, material enclosed within cover 45 is liquid. Thus, should seals in cover 45 fail, or should a failure or puncture occur in cover 45, outer cover 40 will inhibit leakage of fluid into foam pad 26.

For the arrangement shown in FIG. 2, cover 40 comprises a film folded along fold line 47 with cover 45 positioned therein. Edge seals 48 may comprise a variety of types of seals, for example, heat seals or adhesive seals. For the preferred arrangement described and shown, preferably cover 40 is formed from a heat sealable film, and seals 48 comprise heat seals, formed in a conventional manner. Cover 45 also preferably comprises a heat-sealable film. For the arrangement shown in FIG. 2, cover 45, not shown in detail, includes peripheral heat seals 49.

Referring now to FIG. 3, as previously-indicated, substrate 43 is sealed within both outside cover 40 and inside cover 45. Substrate 43 preferably comprises a compressible (under manual pressure), open cell, porous, material such as a foam (for example, polyurethane foam, a rubber sponge or a natural sponge). In preferred embodiments, the substrate 43 provides three basic operations in use: it is soft and compressible, and thus is comfortable to the user of the seat cushion 3; it spreads the mixture 42 over a greater surface area; and, due to its open-cell construction, it will operate as a mechanical re-emulsifier to re-emulsify the mixture 42 during use. Further detail with respect to this re-emulsification is provided hereinbelow, after discussion of the mixture 42.

The fluid mixture 42 comprises mixture of materials to serve two primary purposes in a preferred manner: it is readily heated up upon exposure to microwave energy; and, it will dissipate heat therefrom, in cooling back to ambient, at least in part by a phase transfer of a material in the mixture. By "readily heated up upon exposure to microwave energy" in this context, is meant that it will heat to a selected or preferred temperature, for example, typically to at least 30° C. preferably to 30°-90° C., and usually to a selected point within the range of about 30° C.-65° C., upon exposure to microwave energy in a 700 or 750 watt microwave oven, for a period of 3 to 15 minutes or so.

Preferred operation of the thermal storage unit 20 turns upon utilization of preferred materials both: as the mixture; and, as the internally-received substrate 43. Details with respect to these materials are as follows.

1. The Mixture

Mixtures, used in thermal storage units according to the present invention, comprise a form of solid-in-liquid mixture, for example a "wax-in-liquid" or "oil-in-liquid" emulsion (or a solid in liquid suspension) wherein the wax or oil (solid) phase, at 25° C., is solid; and in which the wax or oil phase (i.e. solid phase), after the arrangement has been sufficiently heated up upon exposure to microwave energy, becomes a liquid. Herein the terms "wax" and "oil" are used interchangeably to refer to the phase which is dispersed in the liquid phase. In typical applications, the "oil phase" in the mixture should comprise a material having a melting point somewhere within the range of about 30°-90° C., more preferably 30°-65° C.

Preferably, the "oil phase" is a material which does not absorb microwave energy. Rather, in typical preferred applications, the oil phase or solid phase within the emulsion 42 is heated up and melted by thermal transfer from the liquid phase.

Principal characteristics to be considered in selecting the material for the "oil phase" concern the following. The melting point of the material should be a melting point at a temperature satisfactory for the use to which the thermal storage unit is to be placed. For example, if the thermal storage unit is utilized as a part of a seat cushion (for example, in an arrangement as shown in FIGS. 1-3) it will be preferred that the material be chosen to have a melting point of at least 40° C., preferably about 50°-60° C., typically and most preferably at around 50°-55° C. Such a temperature is relatively warm, but suitable for an internal storage unit within a seat cushion.

On the other hand, if the thermal storage unit is being utilized in a system more likely to come into closer contact with exposed skin, and relatively sensitive areas of the body, it may be desirable to utilize as the "oil" phase, a material having a lower melting point. For example, if the thermal storage unit is utilized as part of a hand warmer, or foot warmer, for bare hands or bare feet, a melting point on the order of about 30° C.-40° C. may be preferred, since higher temperatures may be uncomfortable for the user.

Other factors to be considered in the selection of the material for the "solid phase" or "oil phase" of the emulsion, concern heat of fusion (or latent heat of melting). In general, the greater the heat of fusion, the greater the amount of heat given off, per unit weight, as the solid phase cools and solidifies. Thus, the better the material will operate as a thermal storage material, since, after having been heated to liquid, a longer period of time, with greater energy lost, will be achieved before the oil phase returns to a solid. Alternatively, the greater the heat of fusion, the more energy or heat the oil phase will be able to store per unit weight, during the initial heating up in the microwave oven.

Another factor to be considered in selecting the material for the "solid phase" or "oil phase" is the ability to form a stable mixture (for example emulsion) with the liquid phase. In general, materials that can relatively readily form an emulsion which is stable over a temperature range on the order of about 0°-90° C., will be preferred. It is anticipated that, for reasons stated hereinbelow, the typical liquid phase will be water; thus, the ability to form an emulsion in water is generally an issue. Preferably, the material for the oil phase is chosen from materials which will readily re-emulsify, should the thermal storage unit be subjected to relatively cold temperatures, with freezing, gelling or some other form of inducement to separation of the two phases of the emulsion.

Paraffin wax is a preferred material for use in thermal storage units according to the present invention, especially when the thermal storage unit is utilized as part of a seat cushion. Paraffin wax is a mixture of solid hydrocarbons having the general formula $C_nH_{2n+2}$ and typically has a melting point somewhere within the range of 45°-60° C. Particular waxes can be selected, for preferred melting points. Thus, a particular paraffin wax can be selected and obtained with a melting point of about 50°-57° C., i.e. 53° C., if desired. Paraffin waxes, in general, exhibit melting points over the preferred ranges for utilization with systems according to the present invention; they readily form emulsions with liquid phases such as water; they are relatively non-toxic; they exhibit desirable heat-storage capabilities; and they are relatively inexpensive and easy to obtain. It is foreseen that derivatives of paraffin wax, such as alkylated paraffins, having similar melting point ranges, may also be used. The term "paraffin wax" as used herein, is meant to include not only materials according to the general formula $C_nH_{2n+2}$, but also modified waxes such as alkylated paraffin wax derivatives of such materials and similar compounds.

Other usable materials in the "oil phase" and systems according to the present invention include: beeswax; (mp. 62°-65° C.); candelilla wax (mp. 68°-70° C.); carnauba wax (mp. 82°-85.5° C.); cotton wax; wool wax; montan wax (mp. 80°-86° C.); and, mixtures of waxes.

A preferred paraffin wax for systems according to the present invention is a fully refined paraffin having a nominal melting point of 53° C.

The liquid phase of the emulsion should comprise a material which readily absorbs microwave energy and, as a result, rapidly heats. Preferably water or water mixtures (such as water/alcohol, water/glycol, or water/glycerol) are used. Water, of course, is also desirable from the point of view of toxicity and cost. In some systems, aqueous solutions of various salts may be desirable for the liquid phase, for example solutions of: calcium chloride, sodium chloride, aluminum sulfate, magnesium bromide or magnesium sulfate. The presence of such salts in the aqueous phase will modify the freezing point of the liquid phase, its heat capacity, and the ability to form the emulsion.

The emulsions may include adjuvants such as: surfactants or emulsifiers, preservatives and/or dyes. These will be discussed in greater detail below.

Preparation of the Mixture (Emulsion)

In general it is the wax phase (solid at room temperature) of the mixture which performs much of the thermal storage function, in emulsions used in thermal storage units according to the present invention. Thus, it will generally be preferred that mixtures utilized in thermal storage units according to the present invention include a relative amount, for example by weight, of solid phase to liquid phase which reflects the least amount of liquid phase needed to suspend or emulsify the amount of solid phase desired for the particular application. The amount of solid phase desired for any given application will depend, of course, upon the size of the thermal storage unit needed; the length of time it is required to remain somewhat warm; and, the conditions under which it is to be used. Generally, mixtures comprising about 40–60% by weight solid phase, the balance comprising liquid phase, surfactant and possibly other adjuvant, will be useful and preferred. The specifics given below for an example of a seat cushion, provide basic principles of operation which can be extended to many other uses.

In general, it is foreseen that mixtures according to the present invention will be prepared by mixing a melt of the solid phase together with the liquid phase, in the presence of an emulsifier or surfactant. The emulsifier or surfactant may comprise any surface activate agent effective, and in an amount effective, to achieve sufficient dispersion of one phase in the other, typically by reducing the surface tension of the oil or wax and providing the oil phase in sufficiently small droplets for the emulsion to form. The particular surfactant utilized may depend upon the solid phase and liquid phase chosen. Many conventional surfactants for mixing oil and aqueous phases can typically be used. When the solid phase comprises paraffin wax and the liquid phase water, acetylene-base surfactants such as the Surfinols available from duPont are desirable surfactants. Other useable surfactants include alkanol amides; alkylaryl sulfonates; amine acetates; amine oxides; sulfonated amines and amides; block polymers; carboxylated alcohol ethoxylates; ethoxylated alkyl phenols; ethoxylated amines and amides; ethoxylated fatty acids; ethoxylated fatty esters and oils; fatty esters; glycerol esters; glycol esters; imidazoline(s); isothionates; lanolin-based surfactants; lecithin(s); olefin sulfonates; phosphate esters; organic phosphorous derivatives; polymeric surfactants (polysacaharides, acrylic acids or acrylamides); propoxylated or ethoxylated fatty acids; propoxylated or ethoxylated alcohols or alkylphenols; soaps; sorbitol derivatives; sulfates and sulfonates of ethoxy alkyl phenols; sulfates and sulfonates of oils and fatty acids; sulfates of alcohols and ethoxylated alcohols; sulfonated benzene, toluene or xylene; and, sulfonates of dodecylbenzene, tridecylbenzene, alkylnaphthalene(s), and, petroleum.

In general, the amount of surfactant utilized should be an amount effective to achieve formation of a stable emulsion. From the specific example of the seat cushion described hereinbelow, a typical formulation will be understood.

Preferably, the emulsion is mixed until the particle size is about 90% (population) less than about 1.6 micrometers and 50% (number) less than about 1.05 micrometers. However, a variety of particle size ranges can be accommodated.

Other Adjuvants

It is foreseen that in some instances other adjuvants may be provided in the mixture. For example, preservatives may be included, to inhibit bacterial growth over the life of the thermal storage unit. For typical systems, for example involving a paraffin wax/water emulsion, preservatives such as chlorobutanol; dichlorobenzyl alcohol; propylene glycol; formaldehyde; phenylmercuric acetate; benzoic acid; chloromethyl isothiazolinone; methyl isothiazolinone; dehydroacetic acid and its sodium salt; potassium sorbate; parabens; sodium pyrothione, zinc pyrothione and glutaraldehyde will be effective to accomplish this. In general, the amount of preservative should be an amount effective to achieve the desired level of resistance to biological activity. The specific formulation given hereinbelow, for a preferred arrangement utilizable as a seat cushion, provides further guidance with respect to this.

Other adjuvants which may be utilized in thermal storage units according to the present invention include: dyes; antioxidants; flame retardants; etc.

Use of the Mixture as a Thermal Storage Material

In use, mixtures according to the present invention operate as thermal storage material, upon activation with microwave energy. In a typical use, the mixture is exposed to sufficient amounts of microwave energy such that the liquid phase is heated to a temperature above the melting point of the "solid" or "oil" phase. In addition, if the solid phase is not microwave active, sufficient energy should be imparted to the liquid phase such that by thermal transfer from the liquid phase to the solid phase, the solid phase (oil phase) is melted.

Upon removal from the microwave oven, the emulsion will be hot. It will undergo three periods of cooling: a period of sensible heat loss (from the original liquid phases) above the freezing point of the oil phase; a period of latent heat loss during transition of the oil phase from a liquid to solid (at about the phase transfer temperature thereof); and, a second sensible heat loss period below the melting point of the solid phase.

The rate of heat loss in the two periods of sensible heat loss will generally be controlled by the heat capacity of the original liquid phases. For a liquid phase such as water, the heat loss will be relatively rapid by comparison to heat loss during the middle stage of transformation in the oil phase from liquid to solid. During the stage of heat loss which occurs during the transformation of the oil phase from a liquid to a solid, heat loss will be controlled by such characteristics as rate of crystallization of oil phase. Thus, it can be seen, that the oil phase serves as a thermal reservoir which will act to retain the emulsion at a relatively constant, warm, temperature, for a significant length of time, by comparison to a system which just utilizes a liquid phase.

Operation of the Foam or Sponge as a Mechanical Re-Emulsifier

As explained above, in preferred embodiments, the mixture comprises an emulsion retained within thermal storage units as a fluid saturating an open cell foam or sponge. As indicated, the open cell foam or sponge provides at least three functions: it adds further cushion to the device, if the device for example is a seat cushion;

it dissipates a given volume of emulsion over a wider area; and, it serves as a mechanical re-emulsifier. The latter function is particularly advantageous.

More specifically, it is foreseen that in some instances thermal storage units according to the present invention may be utilized under conditions such that ambient temperatures are sufficiently low to gel, and to some extent separate, the emulsion once the emulsion has totally cooled. Under such circumstances, the open cell foam or sponge operates as a mechanical re-emulsifier, to re-emulsify the system. In particular, as the liquid pumps through the open cells of the foam or sponge, for example through ordinary manipulating, squeezing, bending or folding of the cushion or thermal storage unit, the mixture of oil (wax) and liquid phase will tend to re-emulsify. This is highly advantageous, as it facilitates re-utilization of thermal storage units according to preferred embodiments of the present invention.

Specific Example of a Working Embodiment

In the following description, a working example of a specific embodiment of the present invention, involving the utilization of a thermal storage unit in the context of a seat cushion, is presented. From the specifics provided, general applications of the present invention in a wide variety of systems can be foreseen and understood.

The following materials are described for use in the context of a seat cushion for use by adults. The seat cushion described will have outer dimensions of about 32 cm×47 cm×3 cm.

The outer sheath for the working example described comprises a nylon fabric (preferably a rip-stop nylon). A specific, useable material is 200 denier Nylon Oxford Taffeta, No. 68205 available from Tapetex Corp., Rochester, N.Y. 14623. Preferably a material is selected which has been subjected to fire-retardant treatment. This material is utilized for the portion of the cushion corresponding to sheath 25, FIG. 3.

The foam envelope, corresponding to foam pad 26, FIG. 3, comprises any conventional seat cushion foam, for example a polyurethane foam slit to form the envelope. Preferably fire-retardant foam is selected. A usable material is L32SX Foam, available from E. R. Carpenter, Templeton, Tex. 76503. The foam envelope is selected with exterior dimensions substantially corresponding to those desired for the overall construction.

The thermal storage unit, as indicated generally above, comprises an outer pouch enclosing an inner pouch, which encloses an open cell foam or sponge saturated with the fluid emulsion. The outside pouch comprises an 8 mil matte two-side vinyl available under the trade name Delta 6 from Flex-Seal Packaging of Rochester, N.Y. The dimensions of the pouch are about 30 cm×42 cm, with a 0.6 cm heat seal along the periphery thereof.

The inside pouch preferably comprises a polymeric laminate, for example, a nylon/high density polyethylene (HDPE)/linear low density polyethylene (LLDPE) copolymer; or, a polypropylene/nylon (coated with polyvinylidene chloride) copolymer. The dimensions of the inside pouch are about 28 cm×39 cm, with a 1.25 cm heat seal around the periphery thereof.

Received inside the inside pouch are the foam substrate (serving the function of the internal mechanical re-emulsifier) and, the emulsion. The foam preferably comprises a material which is not only open cell, but is also stable to the temperatures to which the system will be heated in use; does not hydrolyze under the conditions of use; and, is not appreciably soluble in the organic phase. Preferably polyurethane foam (either polyester or polyether) is used. Generally, polyether foams will be preferred, since they are not as sensitive to hydrolysis as are polyester foams.

A large variety of densities can be selected, for the foam of the re-emulsifier. One foam that is usable as the internal foam is product J32SP available from E. R. Carpenter of Templeton, Tex. 76503. This foam has a density of 0.9/ild: 32–39. A foam pad about 2.2 cm×23 cm×33 cm would be used in the construction being described.

The emulsion used to saturate the foam may comprise a mixture, by weight, as follows: paraffin wax 45–60% (melting point about 55° C.)/surfactant (surfinol) 5–12%/water 30–45%/(preservative) ucracide 250, a gluteraldehyde, available from Union Carbide, 0.1–0.2%; and Proxel GLX (1,2-benzisothiazolin-3-one), 0.1–0.2%.

The paraffin wax (molten) can be, and preferably will have been, blended with the water and surfactant, by high shear mixing, to provide a particle size distribution (by number) in the resulting emulsion of about 90% less than 1.55 microns, 50% less than 1.05 microns, and a viscosity of about 0.913 cp. If desired, the emulsion can be filtered, for removal of large particulate material, before it is placed within the thermal storage unit.

The total amount of emulsion used will be an amount sufficient to saturate the foam received within the internal pouch. For the arrangement described in the drawings, it is anticipated that about 1.14 kg of emulsion would be preferred.

When the emulsion and foam substrate are enclosed within the film (film envelope 45, FIG. 2) it is desirable to apply some vacuum draw to the interior of the film pouch, to reduce air presence and facilitate saturation of the foam with the fluid emulsion.

The construction described is prepared for use by placement in a 700 or 750 watt microwave oven for about three minutes on each side. If simply left standing at about 5°–20° C., it would remain warm for about 10 hours. The actual rate of heat loss in use will depend, of course, upon how much of the time the cushion is used with a person sitting thereon; the size of the person; the ambient temperature; and related factors.

Alternative Applications of Principles According to the Present Invention

The specific arrangement described above, of a heat cushion, involves an arrangement which is intended to radiate heat from an outer surface thereof, to the exterior environment. Thus, the material chosen to enclose the thermal storage unit is a material which will allow the thermal energy to pass toward an outer surface thereof, to warm the user.

It is foreseen that an alternative embodiments, thermal storage units according to the present invention may be enclosed within insulating blankets or the like designed to retain heat therein. For example, such heating constructions might be utilized at hand-warming muffs or foot-warming boots. They may also be utilized, for example, as thermal blankets or the like.

What is claimed is:

1. A thermal storage unit which is activatable by exposure to microwave energy; said thermal storage unit comprising:

(a) a microwave-transparent container; and, (b) a mixture enclosed within said container; said mixture comprising:
  (i) a liquid phase including a microwave active fluid; and
  (ii) a solid phase comprising phase change particles suspended in said liquid phase; and,
(c) a mechanical re-emulsifier received within said container, in contact with said mixture.

2. A thermal storage unit according to claim 1 wherein:
  (a) said liquid phase comprises water; and,
  (b) said solid phase comprises paraffin wax.

3. A thermal storage unit according to claim 1 wherein said container comprises a flexible pouch.

4. A thermal storage unit according to claim 1 wherein said mechanical re-emulsifier comprises a compressible, open-cell, substrate.

5. A thermal storage unit according to claim 1 wherein said solid phase comprises particles having a melting point within the range of 30°–65° C.

6. A thermal storage mixture according to claim 1 wherein said solid phase comprises material having a melting point below that to which said liquid phase is heated, during use.

7. A thermal storage mixture according to claim 1 wherein said solid phase comprises microwave inactive material.

8. A thermal storage mixture according to claim 1 wherein said liquid phase comprises water.

9. A thermal storage mixture according to claim 8 wherein said solid phase comprises organic wax material.

10. A thermal storage mixture according to claim 1 wherein said solid phase comprises wax selected from the group consisting essentially of: paraffin wax; beeswax; candelilla wax; carnauba wax; cotton wax; wool wax; montan wax; and, mixtures thereof.

11. A thermal storage mixture according to claim 1 wherein said solid phase comprises material having a melting point of at least 30° C.

12. A thermal storage mixture according to claim 1 comprising an effective surfactant in an amount effective to maintain said suspension or emulsion.

13. A thermal storage mixture according to claim 12 wherein when said surfactant is selected from the group consisting of acetylene-base surfactants; alkanol amides; alkylaryl sulfonates; amine acetates; amine oxides; sulfonated amines and amides; block polymers; carboxylated alcohol ethoxylates; ethoxylated alkyl phenols; ethoxylated amines and amides; ethoxylated fatty acids; ethoxylated fatty esters and oils; fatty esters; glycerol esters; glycol esters; imidazoline(s); isothionates; lanolin-based surfactants; lecithin(s); olefin sulfonates; phosphate esters; organic phosphorous derivatives; polymeric surfactants (polysacharides, acrylic acids or acrylamides); propoxylated or ethoxylated fatty acids; propoxylated or ethoxylated alcohols or alkylphenols; soaps; sorbitol derivatives; sulfates and sulfonates of ethoxy alkyl phenols; sulfates and sulfonates of oils and fatty acids; sulfates of alcohols and ethoxylated alcohols; sulfonated benzene, toluene or xylene; and, sulfonates of dodecylbenzene, tridecylbenzene, alkylnaphthalene(s), and, petroleum.

14. A heating construction comprising:
(a) an outer cover; and,
(b) a thermal storage unit activatable by exposure to microwave energy; said thermal storage unit being positioned within said outer cover; said thermal storage unit comprising:
  (i) a microwave-transparent container; and,
  (ii) a mixture contained within said container; said mixture comprising; a liquid phase including a microwave active fluid; and, a solid phase comprising phase change particles suspended in said liquid phase, wherein said mixture comprises art emulsion when said suspended particles are heated above their melting point; and,
(c) a mechanical re-emulsifier received within said container, in contact with said mixture.

15. A heating construction according to claim 14 wherein:
  (a) said liquid phase comprises water; and,
  (b) said solid phase comprises paraffin wax.

16. A heating construction according to claim 15 wherein said outer cover comprises a seat cushion.

17. A heating construction according to claim 14 wherein said outer cover comprises a seat cushion.

18. A thermal storage mixture according to claim 14 comprising an effective surfactant in an amount effective to maintain said suspension or emulsion.

19. A thermal storage mixture according to claim 18 wherein when said surfactant is selected from the group consisting of acetylene-base surfactants; alkanol amides; alkylaryl sulfonates; amine acetates; amine oxides; sulfonated amines and amides; block polymers; carboxylated alcohol ethoxylates; ethoxylated alkyl phenols; ethoxylated amines and amides; ethoxylated fatty acids; ethoxylated fatty esters and oils; fatty esters; glycerol esters; glycol esters; imidazoline(s); isothionates; lanolin-based surfactants; lecithin(s); olefin sulfonates; phosphate esters; organic phosphorous derivatives; polymeric surfactants (polysacharides, acrylic acids or acrylamides); propoxylated or ethoxylated fatty acids; propoxylated or ethoxylated alcohols or alkylphenols; soaps; sorbitol derivatives; sulfates and sulfonates of ethoxy alkyl phenols; sulfates and sulfonates of oils and fatty acids; sulfates of alcohols and ethoxylated alcohols; sulfonated benzene, toluene or xylene; and, sulfonates of dodecylbenzene, tridecylbenzene, alkylnaphthalene(s), and, petroleum.

20. A process of storing thermal energy for release over an extended period of time; said process including the steps of:
(a) exposing a mixture to microwave energy; said mixture comprising:
  (i) a liquid phase including a microwave active fluid; and,
  (ii) a solid phase comprising phase change particles suspended in said liquid phase,
(b) said step of exposing said mixture to microwave energy comprising exposing said mixture to microwave energy of appropriate power and for a sufficient period of time to heat said liquid phase to a temperature above the melting point of said solid phase and to melt said solid phase; and,
(c) re-emulsifying said melted solid phase and said liquid phase with a mechanical re-emulsifier.

* * * * *

UNITED STATES PATENT AND TRADEMARK OFFICE
CERTIFICATE OF CORRECTION

PATENT NO. : 5,424,519
DATED : June 13, 1995
INVENTOR(S) : Gideon Salee

It is certified that error appears in the above-indentified patent and that said Letters Patent is hereby corrected as shown below:

On the title page, item [54] and column 1.

"[54] MICROWAVED-ACTIVATED THERMAL STORAGE MATERIAL; AND METHOD" should be -- [54] MICROWAVE-ACTIVATED THERMAL STORAGE MATERIAL; AND METHOD --.

Column 12, line 11, "art" should be -- an --.

Signed and Sealed this

Twenty-sixth Day of December, 1995

Attest:

BRUCE LEHMAN

*Attesting Officer*  *Commissioner of Patents and Trademarks*